(12) United States Patent
Oddos et al.

(10) Patent No.: US 9,387,160 B2
(45) Date of Patent: Jul. 12, 2016

(54) COMPOSITION AND METHOD OF TREATING SKIN CONDITIONS

(75) Inventors: Thierry Oddos, Meudon (FR); Linda Fournier, Pont de L'Arche (FR); Gaelle Bellemere, Bihorel (FR); Sébastien Saclier, Montaure (FR); Anne-Sophie Brillouet, Los Angeles, CA (US)

(73) Assignee: Johnson & Johnson Consumer Holdings France, Moulineaux (FR)

( * ) Notice: Subject to any disclaimer, the term of this patent is extended or adjusted under 35 U.S.C. 154(b) by 963 days.

(21) Appl. No.: 13/140,445

(22) PCT Filed: Dec. 22, 2009

(86) PCT No.: PCT/EP2009/067801
§ 371 (c)(1),
(2), (4) Date: Jun. 17, 2011

(87) PCT Pub. No.: WO2010/072787
PCT Pub. Date: Jul. 1, 2010

(65) Prior Publication Data
US 2011/0251273 A1   Oct. 13, 2011

(30) Foreign Application Priority Data
Dec. 22, 2008   (EP) ..................................... 08291228

(51) Int. Cl.
| | | |
|---|---|---|
| A61K 31/07 | (2006.01) | |
| A61K 8/67 | (2006.01) | |
| A61K 8/06 | (2006.01) | |
| A61K 8/31 | (2006.01) | |
| A61K 8/86 | (2006.01) | |
| A61Q 19/08 | (2006.01) | |

(52) U.S. Cl.
CPC . *A61K 8/671* (2013.01); *A61K 8/06* (2013.01); *A61K 8/062* (2013.01); *A61K 8/31* (2013.01); *A61K 8/86* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 5,438,073 A | 8/1995 | Saurat et al. | |
| 5,484,816 A | 1/1996 | Yanagida et al. | |
| 6,521,237 B2 | 2/2003 | Cole et al. | |
| 6,531,141 B1 | 3/2003 | Marvel | |
| 2001/0055597 A1 | 12/2001 | Liu et al. | |
| 2002/0048591 A1 | 4/2002 | Cole et al. | |
| 2003/0185772 A1 | 10/2003 | Kouzuki et al. | |
| 2003/0232091 A1 | 12/2003 | Shefer et al. | |
| 2004/0022818 A1 | 2/2004 | Cho et al. | |
| 2006/0177392 A1 | 8/2006 | Walden | |
| 2007/0183993 A1 * | 8/2007 | Binder et al. | 424/59 |

FOREIGN PATENT DOCUMENTS

| | | |
|---|---|---|
| CN | 1096847 C | 12/2002 |
| DE | 19820392 A1 | 11/1999 |
| DE | 10063341 A1 | 6/2002 |
| DE | 10146802 A1 | 4/2003 |
| DE | 10152304 A1 | 5/2003 |
| DE | 102006034320 A1 | 1/2008 |
| EP | 0379367 A | 7/1990 |
| EP | 0421333 A | 4/1991 |
| EP | 0578077 A | 1/1994 |
| EP | 0608433 A | 8/1994 |
| EP | 0826366 A2 | 3/1998 |
| EP | 0995433 A1 | 4/2000 |
| EP | 0885000 B1 | 4/2003 |
| EP | 1352638 A1 | 10/2003 |
| EP | 1433477 A2 | 6/2004 |
| EP | 1977743 A1 | 10/2008 |
| GB | 2379386 A | 3/2003 |
| WO | WO 9524179 A1 | 9/1995 |
| WO | WO 98/13018 | 4/1998 |
| WO | WO 03105806 A1 | 12/2003 |
| WO | WO 2008038140 A | 4/2008 |
| WO | WO 2008/070116 A2 * | 6/2008 |
| WO | WO 2007/127158 A2 | 7/2010 |
| WO | WO 2010072787 A2 | 7/2010 |

OTHER PUBLICATIONS

Datebase GNPD [Online] MINTEL; Sep. 1, 2008, Ziaja Sopot Spa: "30+ Active Protective Moisturising Cream", Database accession No. 973640;—& Ziaja—Focus on Skin: "hydro-retinol", Jul. 15, 2013, Retrieved from the Internet: URL:http//www.ziaja.co.uk/slownik,litera:h,t:512.html [retrieved on Jul. 15, 2013].
International Search Report dated Mar. 25, 2011 for corresponding Application No. PCT/EP2009/067801.
European Search Report dated Jun. 22, 2009 for corresponding Application No. 08291228.8.
Wiechers, et al., Formulating for Efficacy, Int J. Cosmetic Science, vol. 26, Jan. 1, 2004, p. 173-182.
Hansch, et al, Partition Coefficients and Their Uses, Chem Rev Dec 1971 (6): p. 525-616.
RetiSTAR Stabilized Retinol, Technical Information BASF, BASF, DE, No. EMM 050428e, Nov. 1, 2008, p. 1-4.
Essential Fatty Acids + Phospholipids + Vitamins, Lipodermol, Jun. 18, 2009, p. 1-2.
Wilkinson, A. M. et al, "Partition Coefficient". (1997) Compendium of Chemical Terminology: IUPAC Recommendations. Oxford: Blackwell Science. Doi:10.1351/goldbook. ISBN 0-86542-684-8. http://goldbook.iupac.org/P04437.htlm.
INCI—Declaration, published in Kosmetik International 2002 (11), 50-53, XP007921002.

\* cited by examiner

*Primary Examiner* — Jeffrey S Lundgren
*Assistant Examiner* — Michael Schmitt

(57) ABSTRACT

This invention relates to compositions containing a retinoid and use of the compositions for treating skin conditions.

5 Claims, 3 Drawing Sheets

Liberation rate

A)

B)

COMPOSITION AND METHOD OF TREATING SKIN CONDITIONS

CROSS-REFERENCE TO RELATED APPLICATIONS

This application is the national stage filing of Application No. PCT/EP2009/067801, filed Dec. 22, 2009, which application claims priority from European Patent Appl. No. 08291228.8, filed Dec. 22, 2008, the disclosure of which is hereby incorporated by reference in its entirety.

FIELD OF THE INVENTION

This invention relates compositions containing a retinoid and use of the compositions for treating skin conditions.

BACKGROUND OF THE INVENTION

Human skin is subject to certain aging processes, some of which are attributable to intrinsic processes (e.g. chronoaging) and some of which are attributable to exogenous factors (e.g., photo-aging). In addition, temporary or lasting changes to the skin can occur, such as acne, greasy or dry skin, keratoses, rosacea, light-sensitivity, inflammation, erythemas, and allergic or autoimmune-reactive reactions, such as dermatosis and photodermatosis.

The consequences of the above can include thinning of the skin, weaker interlacing of epidermis and dermis, and a reduction in the number of cells and the supplying blood vessels. This often results in the formation of fine lines and wrinkles, and pigment defects can occur.

Retinoids have been used for treating skin conditions caused by intrinsic aging, exogenous factors, or skin diseases. Specifically, retinol has been widely used for treating acne and for reducing the appearance of wrinkles, fine lines, stretch marks, and cellulite.

However, despite the beneficial effects of retinoid treatment, retinoids can be irritating. This side effect restricts the use of retinoids.

It is therefore an objective of this invention to provide novel retinoid compositions and methods for the treatment of above-mentioned skin conditions that avoid the adverse effects of retinoid administration. In particular, it has been found that control of the retinoid liberation rate from a cosmetic composition, for example by controlling the polarity of the ingredients in the composition, results in increased retinoid activity and decreased retinoid irritation. We have unexpectedly observed that combining a non-polar emollient with a polar emollient within a range of desirable weight ratios in a retinoid composition significantly reduces the skin irritation of the retinoid and enhances the efficacy of the retinoid.

SUMMARY OF THE INVENTION

This invention relates to oil-in-water emulsion non-foamable cosmetic compositions containing (i) at least one retinoid chosen in the group consisting of retinol, retinal and retinol esters, (ii) at least one polar emollient having a net relative polarity index to the retinoid from about 0.5 to 2, and (iii) at least one non-polar emollient having a net relative polarity index to the retinoid from about 7 to about 10. The weight ratio of said polar emollient to said non-polar emollient is from about 95 to 5 to about 40 to 60.

This invention also relates to oil-in-water emulsion non-foamable cosmetic compositions containing at least one non-encapsulated retinoid chosen in the group consisting of retinol, retinal and retinol esters, wherein the liberation of said retinoid from said composition is from about 1 $\mu g/cm^2$/hour to about 2.6 $\mu g/cm^2$/hour.

This invention further relates to methods for treating acne and for reducing the appearance of wrinkles, fine lines, stretch marks, or cellulite by topically applying a cosmetically effective amount of the compositions of this invention to skin in need of such treatment.

Other features and advantages of this invention will be apparent from the detailed description of the invention and from the claims.

DETAILED DESCRIPTION OF PREFERRED EMBODIMENTS

Figure 1:
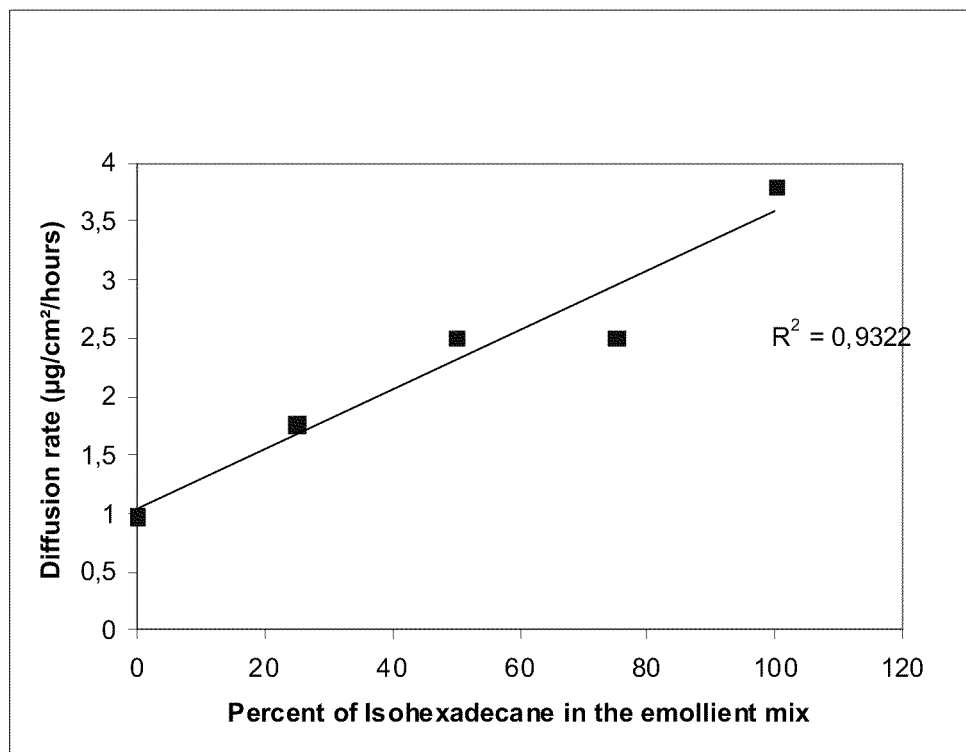
FIG. 1 depicts the relationship between emollient polarity and retinol liberation rate from a cosmetic composition.

Unless defined otherwise, all technical and scientific terms used herein have the same meaning as commonly understood by one of ordinary skill in the art to which the invention belongs. All publications, patent applications, patents, and other references mentioned herein are incorporated by reference. Unless otherwise indicated, a percentage refers to a percentage by weight (i.e., % (W/W)).

As used herein, "topical application" means directly laying on or spreading on the skin, e.g., by use of the hands or an applicator such as a wipe.

As used herein, "cosmetically effective amount" means an amount of a physiologically active compound or composition sufficient for treating acne or for reducing the appearance of wrinkles, fine lines, stretch marks, or cellulite, but low enough to avoid serious side effects. The cosmetically effective amount of the compound or composition will vary with the particular condition being treated, the age and physical condition of the end user, the severity of the condition being treated, the duration of the treatment, the nature of other treatments, the specific compound or product/composition employed, and like factors.

As used herein, "acne" means an inflammatory disease of the hair follicles and sebaceous glands characterized by blackheads, whiteheads, pustules, nodules and, in the more severe forms, by cysts and scarring. The lesions appear on the face, neck, back, chest, and arms.

As used herein, "wrinkle" includes fine line, fine wrinkles, coarse wrinkles. Examples of wrinkles include, but are not limited to, fine lines around the eyes (e.g., "crow's feet"), forehead and cheek wrinkles, frown-lines, and laugh-lines around the mouth.

As used herein, "stretch mark" means pink, reddish or purplish indented streaks that often appear on the abdomen, breasts, upper arms, buttocks and thighs.

As used herein, "cellulite" means pockets of fat, which are trapped and cause dimpling in the skin. The dimpling is irregular and patchy and has been identified with orange peel and cheese skin, It is believed that one skilled in the art can, based upon the description herein, utilize the present invention to its fullest extent. The following specific embodiments are to be construed as merely illustrative, and not limitative of the remainder of the disclosure in any way whatsoever.

Cosmetic Compositions

In one embodiment of the invention, the cosmetic compositions which are non-foamable oil-in-water emulsions contain at least one retinoid chosen in the group consisting of retinol, retinal and retinol esters, at least one polar emollient, and at least one non-polar emollient.

In another embodiment, the cosmetic compositions which are non-foamable oil-in-water emulsions contain a non-encapsulated retinoid chosen in the group consisting of retinol, retinal and retinol esters, wherein the liberation rate of said retinoid from said composition is from about 1 µg/cm$^2$/hour to about 2.6 µg/cm$^2$/hour.

In a further embodiment, the cosmetic composition comprises an oil phase in which at least one retinoid chosen in the group consisting of retinol, retinal and retinol esters is dissolved, and said oil phase preferably has a net relative polarity index to the retinoid from about 0.5 to about 5.

Retinoid

The retinoid as used herein, refers to a class of compounds that possess the biological activity of Vitamin A in the skin.

The retinoid of this invention is chosen in the group consisting of retinol, retinal and retinol esters. Preferred retinoids comprise retinol, retinyl palmitate, retinyl acetate, retinyl proprionate, retinal or mixtures thereof. More preferred are retinol, retinal, or mixtures thereof. Most preferred is retinol. These compounds are well known in the art and are commercially available from a number of sources, e.g., Sigma Chemical Company (St. Louis, Mo.), and Boerhinger Mannheim (Indianapolis, Ind.).

The compositions of this invention may contain a safe and effective amount of the retinoid. The compositions preferably contain from about 0.001% to about 2% of retinoid, more preferably from about 0.01% to about 1% of retinoid, and most preferably from about 0.05% to about 0.5% of retinoid.

In one embodiment, the retinoid is non-encapsulated. That means the retinoid is not contained in or absorbed onto another material. Advantageously, the retinol is not in the form of the RetiSTAR® commercialized by BASF, since it does not need to be stabilized before being used in the composition according to the present invention.

Emollients

The cosmetic compositions comprise at least one polar emollient and at least one non-polar emollient. The polar emollient of this invention preferably has a net relative polarity index to the retinoid from about 0.5 to 2. The non-polar emollient of this invention preferably has a net relative polarity index to the retinoid from about 7 to about 10. The desirable net polarity index to the retinoid of the compositions of this invention is from about 0.5 to about 5. Moreover, the retinoid has a sufficient rate of liberation from the cosmetic composition to the skin while maintaining reduced irritation and enhanced efficacy.

The relative polarity index (RPI) of an emollient is well known by the one skilled in the art. The methodology for its calculation is described in the article published by Wiesher et al. 2004 Int J. Cosmetic Science. 26, 173-182. RPI can be calculated from the octanol/water partition coefficient (K) with:

$$RPI=\log K.$$

Partition coefficient estimations K have been published, for example in:

Leo A, Hansch C, and Elkins D (1971). "Partition coefficients and their uses". Chem Rev 71 (6): 525-616.

Wilkinson, Andrew M.; McNaught, Alan D. (1997). "Partition Coefficient". Compendium of Chemical Terminology: IUPAC Recommendations. Oxford: Blackwell Science. doi:10.1351/goldbook. ISBN 0-86542-684-8. http://goldbook.iupac.org/P0447.html and Sangster, James (1997). Octanol-Water Partition Coefficients: Fundamentals and Physical Chemistry, Vol. 2 of Wiley Series in Solution Chemistry. Chichester: John Wiley & Sons Ltd. pp. 178 pages.

The RPI of retinol is approximatively 1.

The RPI of retinal and retinol esters are well-known by the one skilled in the art and are similar to RPI of retinol.

The net RPI of an emollient to the retinoid is the difference between the Emollient RPI and the Retinoid RPI.

The net RPI of a composition to the retinoid is the difference between the Composition RPI and the Retinoid RPI.

The net RPI of an oil phase to the retinoid is the difference between the Oil Phase RPI and the Retinoid RPI.

As used herein, non-polar emollients of this invention include aromatic or linear esters, guerbet ester, mineral oil, squalane, isohexadecane, squalene, liquid paraffin, and the like.

Preferred non-polar emollients of this invention include isohexadecane, squalane, and mixtures thereof.

As used herein, polar emollients of this invention include, propylene glycol stearyl ether, propylene glycol isostearate, and the like.

Preferred polar emollients include PPG15 stearyl ether, propylene glycol isostearate and mixtures thereof.

According to this invention, the weight ratio of the polar emollient to the non-polar emollient depends a number of factors including the molecular weight of the emollients, the net relative polarity indexes to the retinoid of the emollients, and the solubility of the retinoids. In one embodiment the weight ratio of said polar emollient to said non-polar emollient is from about 95 to 5 to about 40 to 60. The weight ratio of said polar emollient to said non-polar emollient is preferably from about 90 to 10 to about 45 to 55, most preferably from about 85 to 15 to about 50 to 50.

Alternatively, the weight ratio of the polar emollient to the non-polar emollient may be adjusted such that the liberation rate of said retinoid from the cosmetic composition is from about 1 µg/cm$^2$/hour to about 2.6 µg/cm$^2$/hour.

The non-polar and polar emollients constitute from about 0.1% to about 50%, by weight, of the composition, more preferably from about 1% to about 40% by weight of the composition, and most preferably from about 2% to about 25% by weight of the composition.

Cosmetically Acceptable Carriers

One or more cosmetically acceptable carriers may also be present in the cosmetic compositions of this invention.

As used herein, "cosmetically acceptable" means suitable for use in contact with tissues (e.g., the skin) without undue toxicity, incompatibility, instability, irritation, allergic response, and the like, commensurate with a reasonable benefit/risk ratio.

Suitable carriers of this invention include, but are not limited to, water, ethanol, isopropanol, 1,2-propanediol, glycerin, benzyl alcohol, dimethylisosorbide, triacetin, glycol ethers, propylene glycol and polyethylene glycol (PEG). Particularly preferred solvents include PEG having an average molecular weight between about 200 and about 400, castor oil, triacetin, dimethylisosorbide, ethanol, and water, and combinations thereof. The cosmetically acceptable carrier constitutes from about 50% to about 99.99%, by weight, of the composition, more preferably from about 80% to about 95%, by weight, of the composition.

Various compounds may be added to the formulation to alter osmolarity and/or pH to acceptable levels. These include, but are not limited to, mannitol, sucrose, calcium chloride, sodium chloride, sodium phosphate monobasic, sodium phosphate dibasic, sodium hydroxide, and hydrochloric acid.

The compositions may be made into a wide variety of cosmetic articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like.

These product types may contain several types of cosmetically acceptable carriers including, but not limited to solutions, suspensions, emulsions such as microemulsions and nanoemulsions, gels, solids and liposomes. Other carriers can be formulated by those of ordinary skill in the art.

Emulsifier System

Any Emulsifier System cosmetically acceptable can be used in order to obtain the water-in-oil emulsion according to the present invention. The Emulsifier System has only a low impact on the retinoid liberation rate.

Advantageously, the Emulsifier System is chosen in the group consisting of
a) Steareths, in particular of Steareth 21, Steareth 2 and mixture thereof, (such as Brij 72 3%/Brij 721 2%);
b) Glyceryl Stearate, Cetyl Alcohol, Stearyl Alcohol, Behenyl Alcohol, Palmitic Acid, Stearic Acid, Hydroxyethyl Ceteara-midopropyldimonium Chloride and mixture thereof, in particular Prolipid 151 4% and
c) Cetearyl alcohol/Ceteareth-20, Ceteareth-20/Stearyl alcohol and/or mixture thereof, in particular Promulgen G and Promulgen D.

More advantageously the Emulsifier System is a mixture of Cetearyl alcohol/Ceteareth-20, Ceteareth-20/Stearyl alcohol.

Additional Cosmetically Active Agents

In one embodiment, the compositions according to this invention may further contain one or more additional cosmetically active agent(s) as well as the above-mentioned components. A "cosmetically active agent" is a compound, which may be a synthetic compound or a compound extracted, isolated, purified or concentrated from a natural source, or a natural extract containing a mixture of compounds, that has a cosmetic or therapeutic effect on the tissue, including, but not limited to: anti-microbial agents such as anti-yeast, anti-fungal, and anti-bacterial agents, anti-inflammatory agents, anti-aging agents, anti-parasite agents, antioxidants, keratolytic agents, nutrients, vitamins, minerals, energy enhancers, pH-changing agents and the like.

Examples of vitamins that may be constituents of the compositions of this invention include, but are not limited to, vitamin A, vitamin Bs such as vitamin B3, vitamin B5, vitamin B7 and vitamin B12, vitamin C, vitamin K, vitamin E such as alpha, gamma or delta-tocopherol, and their derivatives (such as salts and esters) and mixtures thereof.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, different types of tocopherols (e.g., alpha-, gamma-, and delta-tocopherols and their esters such as acetate) and their mixtures, tocotrienols. Natural extracts containing antioxidants suitable for use in the compositions of this invention include, but are not limited to, extracts containing flavonoid, isoflavonoid, and their derivatives such as genistein and diadzein (e.g., such as soy and clover extracts, extracts containing resveratrol and the like).

Advantageously, the composition according to the present invention does not contain ubiquinone.

More advantageously, the composition according to the present invention does not contain any vitamin D, in particular vitamin D3.

In an advantageous embodiment, the composition according to the present invention does not contain any additional cosmetically Active Agents.

Other Materials

Various other materials may also be present in the compositions. These include proteins and polypeptides, preservatives and an alkaline agent. Examples of such agents are disclosed in the 2008 International Cosmetic Ingredient Dictionary and Handbook, 12th Edition published by the Personal Care Products Council.

In one embodiment, the retinoid is dissolved in the oil phase of the composition and such oil phase has a net relative polarity index to the retinoid from about 0.5 to about 5. The ingredients in the oil phase of the composition are chosen and combined in appropriate weight or molar ratios to achieve the desired oil phase net relative polarity index.

In another embodiment, the retinoid is non-encapsulated and the liberation of said retinoid from said composition is from about 1 µg/cm$^2$/hour to about 2.6 µg/cm$^2$/hour. This may be achieved, for example by employing the polar and non-polar emollients having net relative polarity index to the retinoid from about 0.5 to 2 and 7 to 10, respectively, as described herein The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

All percentages are by weight unless otherwise stated.

EXAMPLES

Example 1

Cosmetic Compositions

Tables 1 and 2 show examples of compositions according to the invention.

TABLE 1

| Ingredient | Emollient 7% (w/w %) | Emollient 7% (w/w %) | Emollient 20% w/w % | Emollient 20% w/w % |
| --- | --- | --- | --- | --- |
| Aqua | QSP | QSP | QSP | QSP |
| Carbomer | 0.4 | 0.4 | 0.4 | 0.4 |
| Disodium EDTA | 0.1 | 0.1 | 0.1 | 0.1 |
| Methyl Paraben | 0.2 | 0.2 | 0.2 | 0.2 |
| Propyl Paraben | 0.15 | 0.15 | 0.15 | 0.15 |
| Phenoxyethanol | 0.5 | 0.5 | 0.5 | 0.5 |
| Sodium Hydroxyde | 1 | 1 | 1 | 1 |

TABLE 1-continued

| Ingredient | Emollient 7% (w/w %) | Emollient 7% (w/w %) | Emollient 20% w/w % | Emollient 20% w/w % |
|---|---|---|---|---|
| Glyceryl Stearate; PEG-100 Stearate | 2 | 2 | 2 | 2 |
| BHT | 0.1 | 0.1 | 0.1 | 0.1 |
| Cetyl Alcohol | 1 | 1 | 1 | 1 |
| Isohexadecane | 3.5 | 0.5 | 10 | 0.5 |
| PPG-15 Stearyl Ether | 3.5 | 7 | 10 | 20 |
| Retinol | 0.115 | 0.115 | 0.115 | 0.115 |
| Polysorbate 20 | 0.135 | 0.135 | 0.135 | 0.135 |
| Ascorbic Acid | 0.05 | 0.05 | 0.05 | 0.05 |

TABLE 2

| Ingredient | % w/w |
|---|---|
| Aqua | QSP |
| Ammonium Acryloyldimethyltaurate/VP Copolymer | 0.50 |
| Disodium EDTA | 0.10 |
| Allantoin | 0.10 |
| Glycerin | 5.0 |
| Butylene Glycol | 2.0 |
| Caprylyl Glycol | 0.50 |
| Methylparaben | 0.250 |
| PEG-8 | 5.0 |
| Dihydroxymethylchromone | 0.10 |
| Cetearyl Alcohol; Ceteareth-20 | 3.0 |
| Stearyl Alcohol; Ceteareth-20 | 3.0 |
| Ethylhexyl Methoxycinnamate | 2.0 |
| Isohexadecane | 1.5 |
| PPG-15 Stearyl Ether | 4.5 |
| Pentaerythrityl Tetraoctanoate | 7.0 |
| *Butyrospermum Parkii* (Shea Butter) | 1.0 |
| Tocopheryl Acetate | 0.25 |
| BHT | 0.1 |
| Dimethicone | 2.0 |
| Cyclohexasiloxane; Cyclopentasiloxane | 2.0 |
| Cocoglycerides; Distearyl Ether; Glyceryl Laurate; Glyceryl Stearate SE; Myristyl Alcohol; Stearyl Alcohol | 1.5 |
| Phenoxyethanol | 0.6 |
| Ethylparaben | 0.15 |
| Propylparaben | 0.15 |
| Polyacrylamide; C13-14 Isoparaffin; Laureth-7; Water | 2.0 |
| Hydroxyphenyl Propamidobenzoic Acid; Butylene Glycol; Pentylene Glycol | 1.0 |
| Nylon-12 | 3.0 |
| Hyaluronic Acid; Water | 0.1 |
| Ascorbic Acid | 0.05 |
| Retinol | 0.115 |
| Polysorbate 20 | 0.135 |
| Sodium Hydroxide | 0.0277 |

The composition in Table 2 was prepared as follows.
Water phase: Water, disodium EDTA, and ammonium acryloyldimethyltaurate/VP copolymer were mixed. Then glycerin and butylene glycol were added.
Premix 1: Dihydroxymethylchromone and PEG-8 weremixed and heated to 80° C. for 10 minutes then cooled down.
Oily phase: Cetearyl alcohol, ceteareth-20, stearyl alcohol, ceteareth-20, ethylhexyl methoxycinnamate, PPG-stearyl ether, isohexadecane, pentaerythrityl tetraoctanoate, butyrospermum parkii (shea butter), tocopheryl acetate, BHT, dimethicone, cocoglycerides, distearyl ether, glyceryl laurate, glyceryl stearate SE, myristyl alcohol, stearyl alcohol, phenoxyethanol, ethyl paraben, propyl paraben, and hyaluronic acid were mixed.
Emulsion: The water phase was added to the oily phase. At 75° C., polyacrylamide, C13-14 isoparaffin, laureth-7, cyclohexasiloxane, and cyclopentasiloxane were added. The mixture was cooled to 30° C., then powders Nylon-12, hydroxyphenyl propamidobenzoic, ascorbic acid, retinol, and fragrance were added and the pH was adjusted with sodium hydroxyde. Premix 1 was then added.

Example 2

Effect of Emollients on the Rate of Retinol Liberation

Compositions that liberated retinol at different rates in vitro were prepared by varying the weight ratio of the polar and non-polar emollients contained therein. This was done by solubilizing retinol in a mixture of two emollients of different polarities: PPG15 stearyl ether having a net relative polarity index to retinol of (i.e., having the same polarity as retinol) and isohexadecane, having a net relative polarity index to retinol of 9.11. The total concentration of emollients in each composition was 7%; however the ratios of the two emollients were different. The compositions (Formulations A-E) are shown in Table 4.

TABLE 4

| | Formulation (w/w %, ROL 0.1%) | | | | |
|---|---|---|---|---|---|
| Ingredient | A | B | C | D | E |
| Aqua | QSP | QSP | QSP | QSP | QSP |
| Carbomer | 0.4 | 0.4 | 0.4 | 0.4 | 0.4 |
| Disodium EDTA | 0.1 | 0.1 | 0.1 | 0.1 | 0.1 |
| Methyl Paraben | 0.2 | 0.2 | 0.2 | 0.2 | 0.2 |
| Propyl Paraben | 0.15 | 0.15 | 0.15 | 0.15 | 0.15 |
| Phenoxyethanol | 0.5 | 0.5 | 0.5 | 0.5 | 0.5 |
| Sodium Hydroxyde | 1 | 1 | 1 | 1 | 1 |
| Glyceryl Stearate; PEG-100 Stearate | 2 | 2 | 2 | 2 | 2 |
| BHT | 0.1 | 0.1 | 0.1 | 0.1 | 0.1 |
| Cetyl Alcohol | 1 | 1 | 1 | 1 | 1 |
| Isohexadecane | 0 | 1.75 | 3.5 | 5.25 | 7 |
| PPG-15 Stearyl Ether | 7 | 5.25 | 3.5 | 1.75 | 0 |
| Retinol | 0.115 | 0.115 | 0.115 | 0.115 | 0.115 |
| Polysorbate 20 | 0.135 | 0.135 | 0.135 | 0.135 | 0.135 |
| Ascorbic Acid | 0.05 | 0.05 | 0.05 | 0.05 | 0.05 |

The in vitro liberation rate of retinol from Formulations A-E is shown in Table 5. The rate was assessed by measuring the diffusion of retinol through a porous membrane of cellulose acetate soaked in myristyl myristate and mounted in a Franz cell. The diffusion of retinol through the membrane into the receptor fluid was monitored over a 24 hour-period. Rate of retinol liberation from the formulation was calculated in $\mu g/cm^2/hours$.

TABLE 5

| | Rate of retinol liberation ($\mu g/cm^2/hours$) |
|---|---|
| Formulation A | 1.395 |
| Formulation B | 1.767 |
| Formulation C | 2.502 |
| Formulation D | 2.514 |
| Formulation E | 3.802 |

Example 3

Effect of Retinol Liberation Rate on Retinol Activity

The additional formulations, Formulations F-H, were prepared. The amount of retinol in each formulation was adjusted such that the formulations delivered the same amount of retinol after 24 hours of application but at different rates. The compositions of Formulations F-H are shown in Table 6.

TABLE 6

|  | Retinol (wt %) | PPG15 Stearyl ether (wt %) | Isohexadecane (wt %) | Emollient ratio (non polar/polar) |
|---|---|---|---|---|
| Formula F | 0.115% | 0% | 7% | 7/0 |
| Formula G | 0.226% | 3.5% | 3.5% | 1/1 |
| Formula H | 0.306% | 7% | 0% | 0/7 |

Retinol activity was measured by assessing the expression of two gene markers relevant for retinoid activity in the epidermis, the Heparin Binding Epidermal Growth Factor (HB-EGF) and the Cellular Retinoic Acid Binding Protein 2 (CRABP2). The retinol irritation effect was measured by assessing the expression of a marker for skin subchronic irritation, interleukin 8 (IL8). Formulations F-H were applied to human skin explants for 24 hours and gene expression was measured in the epidermis by quantitative PCR.

Figure 2:
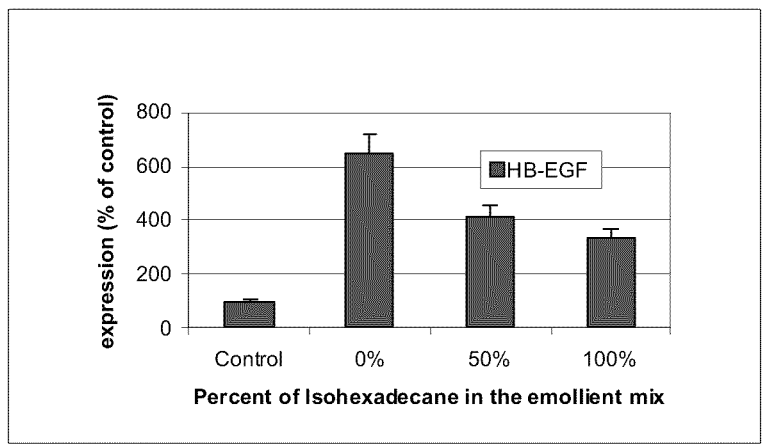
FIG. 2A (HB EGF expression in human skin explant) and 2B (CRABPII expression in human skin explant) depict the relationship between activity of retinol and isohexadecane level in a human skin explant model.
Figure 2:
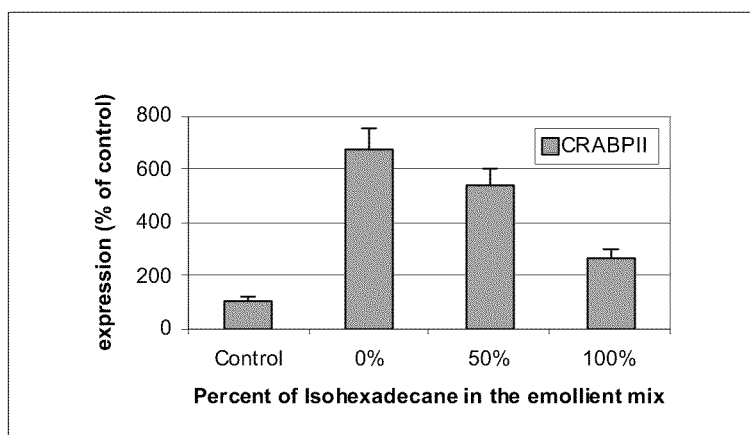

FIGS. 2A and 2B show that the retinol activity measured in the skin explant model was higher in the formulations delivering retinol more slowly. Formulation H had the highest retinol activity.

Figure 3:
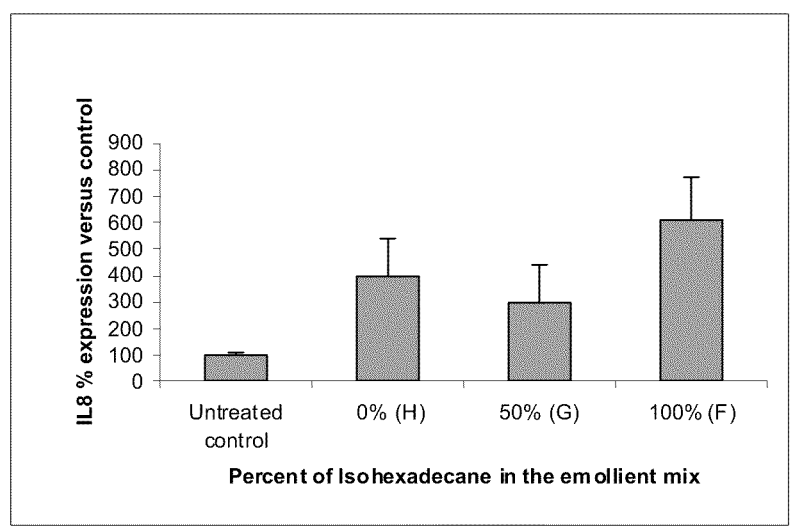
FIG. 3 depicts the relationship between irritation from retinol (IL8 expression after 24 hours of treatment) and isohexadecane level in a human explant model.

FIG. 3 shows that retinol irritation potential was higher in the product delivering retinol rapidly. Formulation F had the highest retinol irritation potential.

The tolerance profiles of Formulations F-H were assessed by a repeated insult patch test on 60 human volunteers. This test consisted in the repeated applications of the formulations under a semi occlusive patch three times a week during the three-week study. After the removal of the patch a redness score was given (mRIPT score). At the end of three weeks all the redness scores were added to give a final redness score.

The results are shown in Table 7. The formulations having a slower delivery of retinol showed a better tolerance profile.

TABLE 7

|  | MRIPT Score |
|---|---|
| Formulation F | 443 |
| Formulation G | 70.5 |
| Formulation H | 69.5 |

What is claimed is:

1. An oil-in-water emulsion non-foamable cosmetic composition comprising: (i) about 0.05 to about 0.5% by weight retinol; (ii) propylene glycol stearyl ether; and (iii) isohexadecane, wherein the weight ratio of propylene glycol stearyl ether to isohexadecane is from about 75:25 to about 50:50, and the composition does not contain any additional active agents other than retinol.

2. The composition according to claim 1 comprising about 2% to about 25% by weight of propylene glycol stearyl ether and isohexadecane combined.

3. The composition according to claim 1, wherein the weight ratio of propylene glycol stearyl ether to isohexadecane is about 75:25.

4. A method for reducing the appearance of wrinkles, fine lines, stretch marks, or cellulite comprising topical application of the composition according to claim 1 to a subject in need thereof.

5. A method for reducing the appearance of wrinkles, fine lines, stretch marks, or cellulite comprising topical application of the composition according to claim 3 to a subject in need thereof.

* * * * *